US008100867B2

(12) United States Patent
Liepold

(10) Patent No.: US 8,100,867 B2
(45) Date of Patent: Jan. 24, 2012

(54) NEEDLE

(76) Inventor: Gerhard Liepold, Watchung, NJ (US)

(*) Notice: Subject to any disclaimer, the term of this patent is extended or adjusted under 35 U.S.C. 154(b) by 408 days.

(21) Appl. No.: 11/914,627

(22) PCT Filed: May 17, 2006

(86) PCT No.: PCT/IE2006/000059

§ 371 (c)(1),
(2), (4) Date: Aug. 8, 2008

(87) PCT Pub. No.: WO2006/123319

PCT Pub. Date: Nov. 23, 2006

(65) Prior Publication Data

US 2008/0294121 A1 Nov. 27, 2008

(30) Foreign Application Priority Data

May 17, 2005 (IE) .................................. S2005/0325

(51) Int. Cl.
*A61M 5/00* (2006.01)

(52) U.S. Cl. ....................................... 604/246; 604/272

(58) Field of Classification Search .......... 604/272–279, 604/246

See application file for complete search history.

(56) References Cited

U.S. PATENT DOCUMENTS

| | | | | |
|---|---|---|---|---|
| 4,917,274 | A * | 4/1990 | Asa et al. | 222/420 |
| 5,223,225 | A | 6/1993 | Gautsch | |
| 6,305,585 | B1 | 10/2001 | Saint-Ramon et al. | |
| 6,551,557 | B1 | 4/2003 | Rose et al. | |
| 6,562,012 | B1 | 5/2003 | Brown et al. | |
| 2002/0143293 | A1 | 10/2002 | Francavilla et al. | |

FOREIGN PATENT DOCUMENTS

| | | |
|---|---|---|
| GB | 2164585 | 3/1986 |

* cited by examiner

*Primary Examiner* — Kevin C Sirmons
*Assistant Examiner* — Imani Hayman
(74) *Attorney, Agent, or Firm* — Hoffman & Baron, LLP

(57) ABSTRACT

A needle (1, 100, 110) for precision filling of dosage containers, such as vials, ampoules etc. is provided. The needle ideally comprises an elongate plastics body (2) having a through channel (5) extending between inlet (3) and outlet (4) openings. A tip portion (7*b*) at the outlet opening (4) has a chamfer (8) tapering towards the outlet opening (4) and an end surface (9) around the opening so that the tip portion (7*b*) is frusto-conical. The surface area of the end surface (9) is sufficiently smaller than the area of the cross-section of the needle body (2) so that in use the needle (1) is capable of providing for formation of smaller droplets of liquid at the outlet (4) compared to needles without such body thickness reduction at the time when the liquid flow through the needle is shut off. The end surface (9) may be so narrow as to take the form of a sharp rim.

8 Claims, 4 Drawing Sheets

X
Y
1
2
2a
3
4
5
6
6a
6b
7
7a
7b
8
9
10
10a
100
110

NEEDLE

CROSS-REFERENCE TO RELATED APPLICATIONS

This application is the National Stage of International Application No PCT/IE2006/000059, filed May 17, 2006, which claims the benefit of Irish Application No. IE S2005/0325, filed May 17, 2005, the contents of which is incorporated by reference herein.

TECHNICAL FIELD

The present invention relates to a needle and in particular to a needle for transfer of liquid to a receptacle such as a vial, ampoule, etc.

BACKGROUND ART

In the pharmaceutical industry it is known to use filling needles for precision transfer of liquids into dosage containers such as vials or ampoules or the like. During such transfer, liquid is supplied at a constant flow rate into the needle channel at one end of the needle and the liquid exits the channel at the other end of the needle. The liquid exits the needle in a continuous stream. In some applications disposable plastics needles are preferred in place of sterilisable metal needles. The nature of plastics materials used for manufacture of disposable needles, and in particular, difficulty in obtaining plastic needles having the same strength characteristics as metal needles gives rise to problems such as control of size and behaviour of liquid droplets which may form at the needle tip at the time when the liquid stream is shut off. Those droplets subsequently separate from the needle tip and fall into the dosage container. This can affect the accuracy of filling dosage containers.

An object of the present invention is to seek to alleviate these problems.

SUMMARY OF THE INVENTION

Accordingly, the present invention provides a needle comprising an elongate body having a liquid inlet end, a liquid outlet end and a through passage defined by a wall and extending between the ends, the body comprising a tip portion at the outlet end thereof, the wall thickness of which is reduced compared to that of the body.

During a process of filling a dosage container using a filling needle, droplets of liquid may form at the needle tip when the liquid stream is shut off. It has been found that a needle having a tip with such a reduced wall-thickness about the channel opening enables the formation of smaller droplets in comparison with those formed at an opening of a needle having uniform wall thickness thereby increasing the accuracy of a fill. It has also been found that such smaller droplets are less likely to separate from the needle and affect the fill accuracy.

Preferably, the reduction of wall thickness at the tip portion of the needle body is provided by forming a chamfer at the tip portion, the chamfer comprising an outer surface of the tip portion converging towards the opening at the outlet end of the body. In one embodiment, an end surface is formed about the opening at the outlet end so that the needle tip is frustoconical. Alternatively and more preferably, the needle tip may take the shape of a sharp rim.

Conveniently, an inlet fitting is provided at the inlet end of the body for connecting the needle to a separate liquid source.

In a most preferred arrangement, the needle material is a polymeric material, i.e. material selected from a silicone or a plastics material, such as, for example, polyethylene, polyetherimide, polysulfone and ethylene tetrafluoroethylene.

Ideally, the thickness of the wall material of the body of the needle is selected sufficient to provide the needle with the same strength and flexibility characteristics as those of a metal needle having substantially the same body length and substantially the same cross-sectional dimensions of the through passageway.

Optionally, the needle material is a metal, such as, for example, stainless steel.

The invention also provides a filling system comprising at least one liquid source vessel having at least one outlet opening, at least one discharge manifold having a first end connected to the outlet opening of the liquid source vessel and a second end connected to the liquid inlet end of the needle, the manifold further comprising a liquid flow control means.

The invention also provides a method of transferring liquid into a vessel using the described above filling system comprising the steps of:

a) directing the outlet end of the needle into a vessel;
b) adjusting the liquid flow control means to cause liquid flow from the liquid source through the discharge manifold and through the passage in the needle at a selected flow rate.

In a most preferred arrangement, the material of the liquid source vessel, the discharge manifold, the liquid flow control means and the needle is selected from a polymeric material, such as a silicone or a plastics material, and the method comprises the step of prior to step a), subjecting the filling system to sterilisation using gamma-rays, the irradiation dose provided by the gamma-rays being such that it enables through-sterilisation of the liquid source vessel, the polymeric material of the discharge manifold, the liquid flow control means and the needle without damaging the polymeric material thereof.

The invention will now be described with reference to the accompanying drawings which show, by way of example only, embodiments of a needle according to the invention.

Figures 1, 2, 3, 3A, 4, 5, 6, 7:
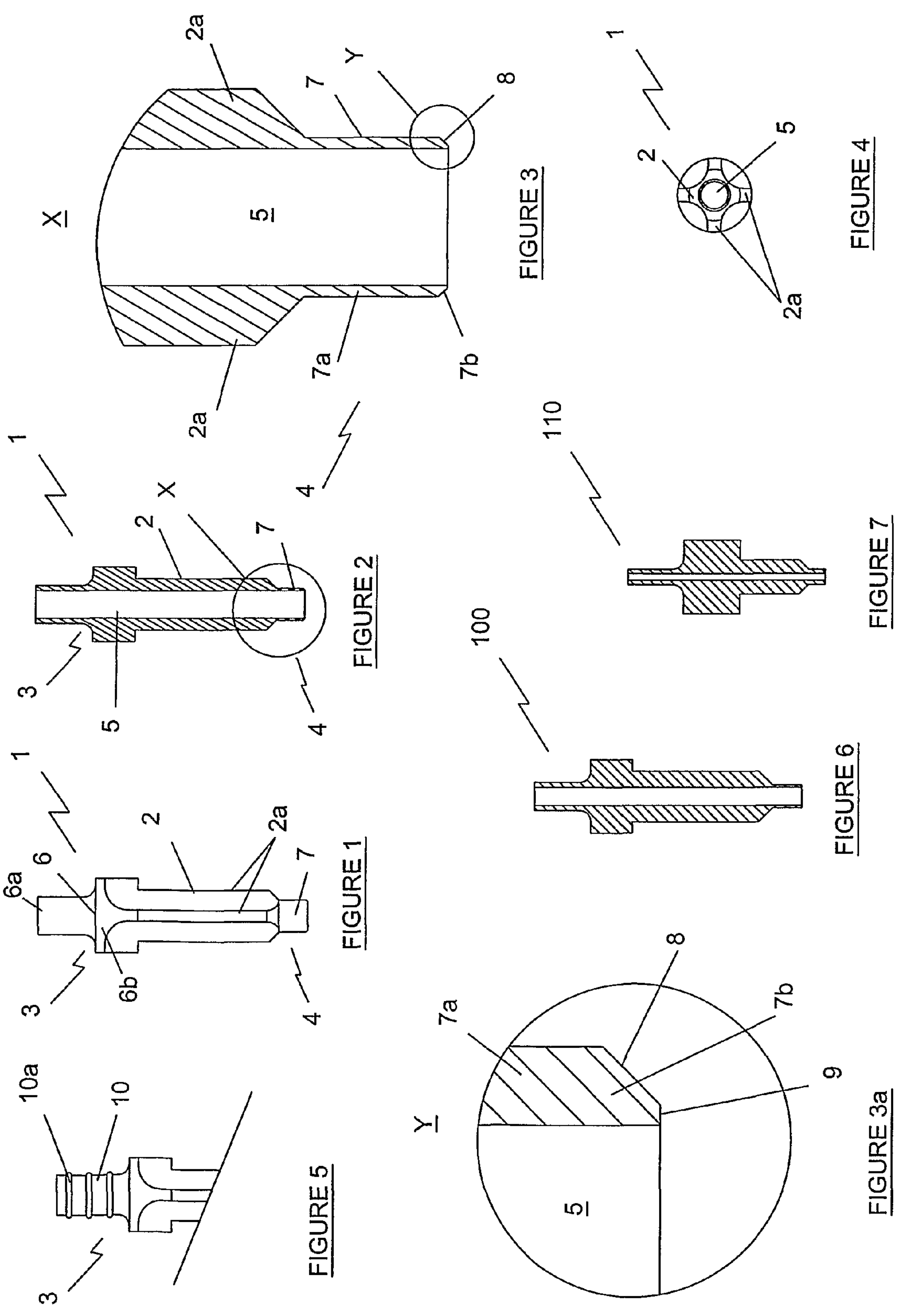
FIG. 1 is an elevation of a filling needle according to the invention.
FIG. 2 is a cross-sectional elevation of the needle of FIG. 1.
FIG. 3 is an enlarged view of area X of FIG. 2 showing an outlet end of the needle in detail.
Figures 8, 8A:
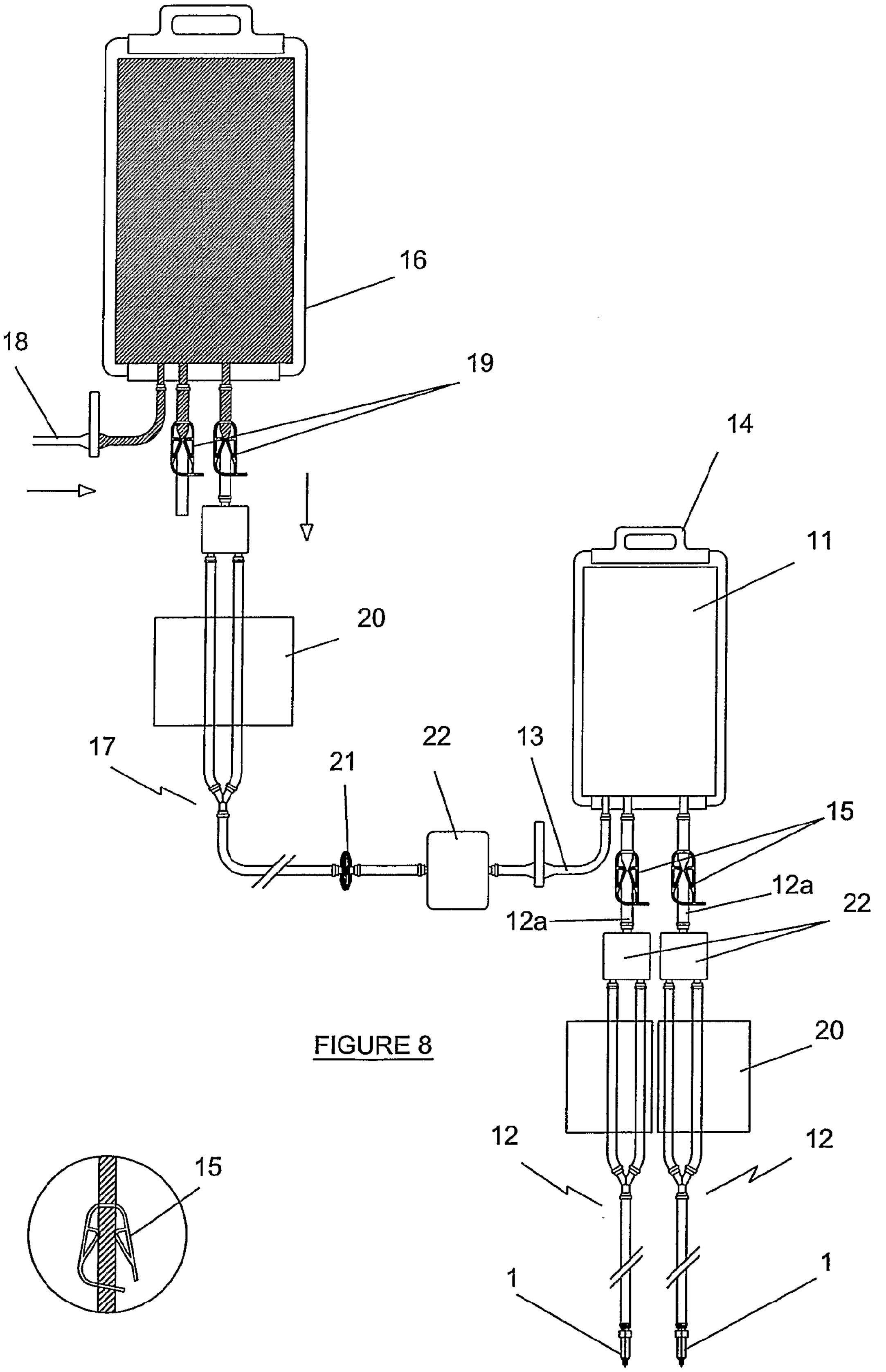
Figure 9:
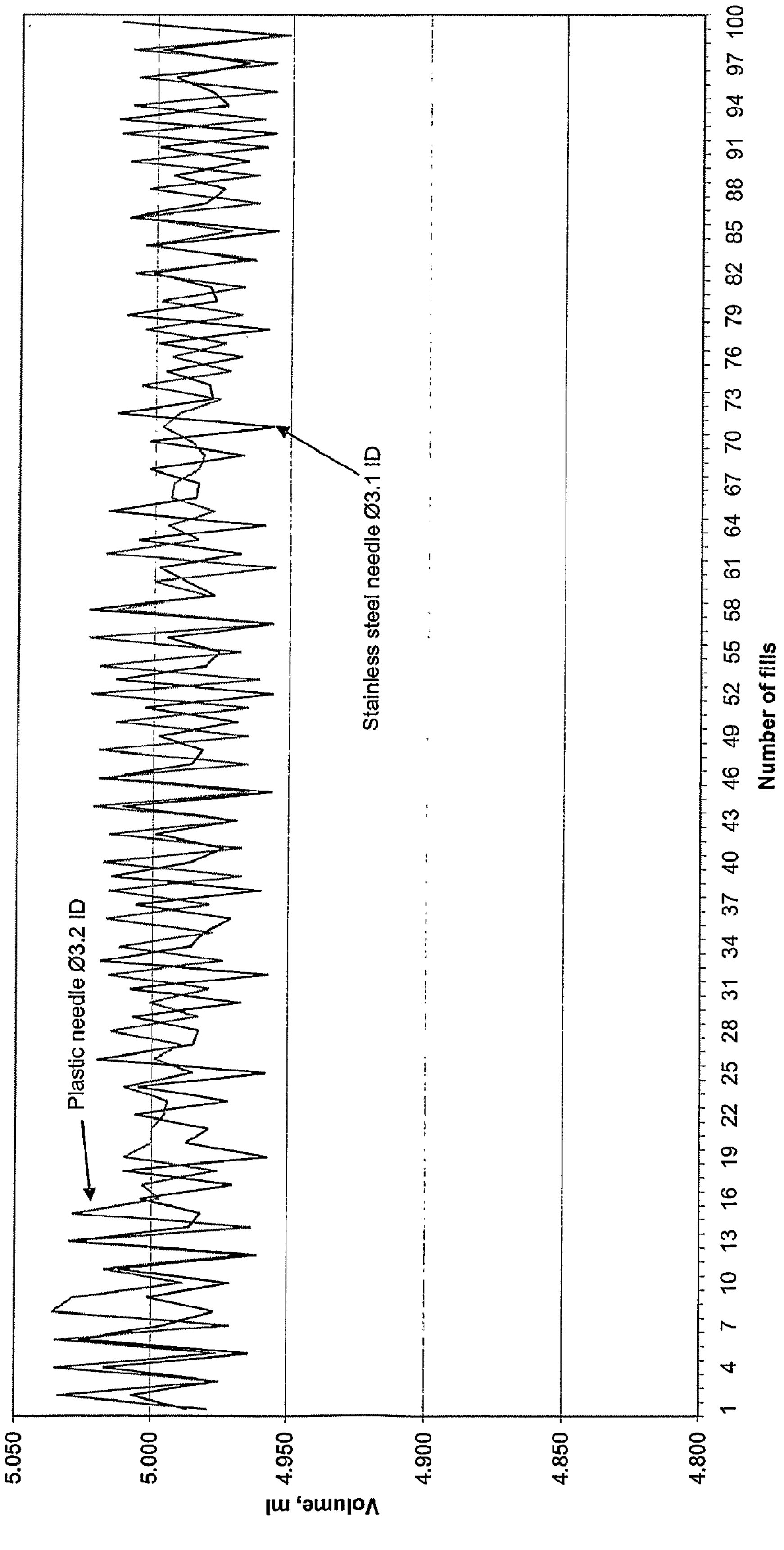
Figure 10:
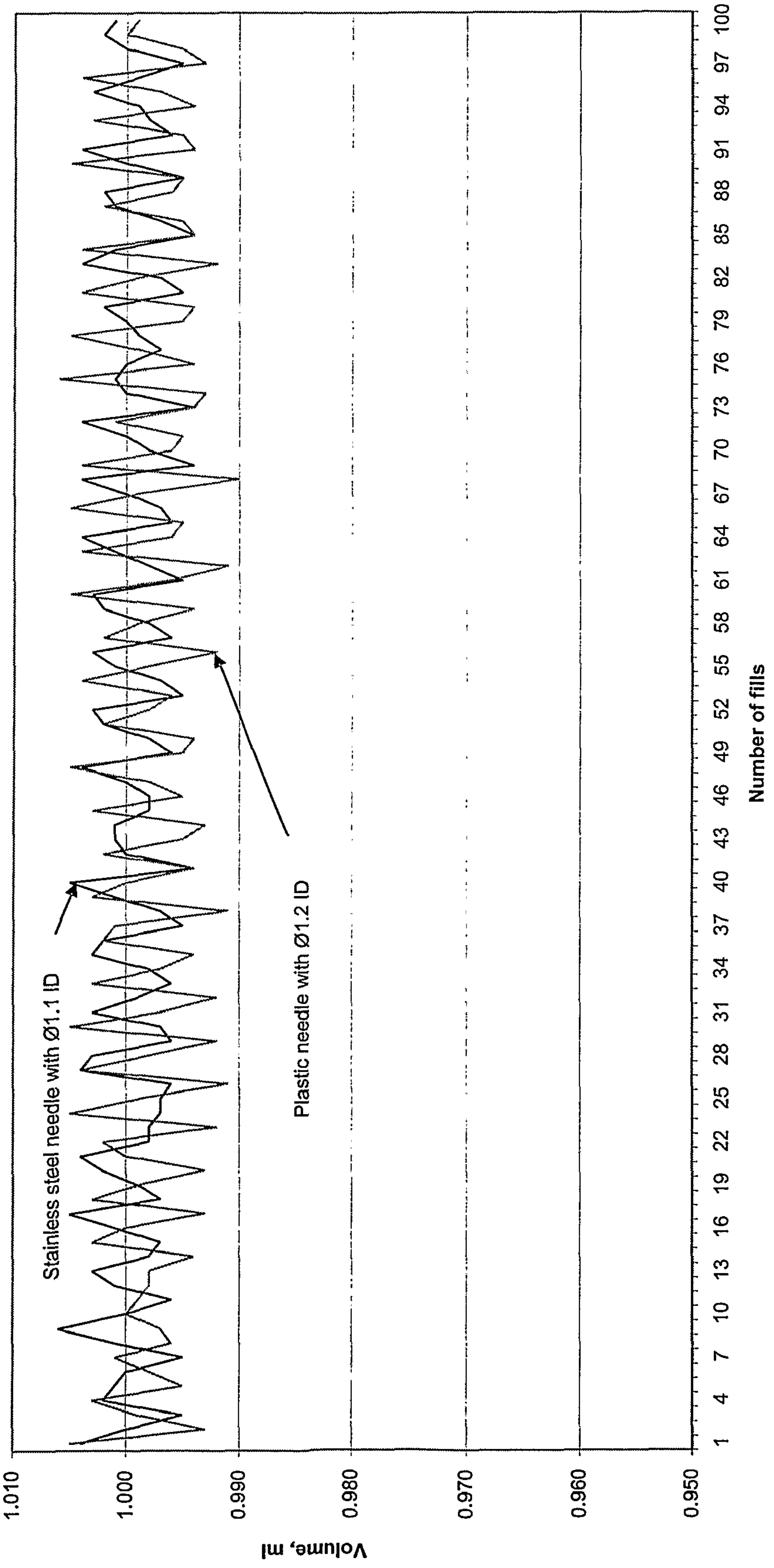

FIG. **3*a* is an enlarged area Y of FIG. 3** showing a chamfered area of the needle in detail;

FIG. 4 is a plan view of the needle of FIG. 1;

FIG. 5 is an elevation of a variant of an inlet fitting at one end of the needle;

FIGS. 6 and 7 are cross-sectional elevations of preferred embodiments of needles similar to that of FIG. 1 but having different sizes;

FIG. 8 is a schematic view showing a pair of filling needles according to the invention connected to a filling system assembly;

FIG. **8*a* is an enlarged view of a lock clip of the filling system of FIG. 8**;

FIG. 9 is a comparative graph illustrating performances of a plastics needle according to the invention having an internal diameter of 3.2 mm and a stainless steel needle having an internal diameter of 3.1 mm; and FIG. 10 is a comparative graph illustrating performances of a plastics needle according to the invention having an internal diameter of 1.2 mm and a stainless steel needle having an internal diameter of 1.1 mm;

MODES OF CARRYING OUT THE INVENTION

A filling needle according to the invention will now be described with reference to the drawings. The most preferred embodiments are illustrated in FIGS. 6 and 7.

Preferred materials for manufacture of the needle are polymeric materials suitable for manufacture of disposable needles, such as for example silicone or polyethylene. The most preferred materials are polyetherimide (PEI), polysulfone (PSU) and ethylene tetrafluoroethylene (ETFE). Plastics needles typically have thicker walls than similar needles made of metal so that the needle shaft will have strength and flexibility characteristics similar to a metal shaft.

Although the present invention is directed to overcoming problems associated with plastics needles, it will be appreciated that the needle of the invention is not limited to plastics materials, and other suitable materials may be used, for example metals, including stainless steel.

Referring to FIGS. 1 to 5, the needle 1 of a first embodiment comprises an elongate body 2 having an inlet end 3, an outlet end 4 and a through channel 5 defined by a wall extending between the ends. The inlet end 3 comprises an inlet fitting 6 having a cylindrical connector portion 6*a* and a collar portion 6*b* intermediate the connector portion 6*a* and the body 2. The inlet fitting 6 is connectable to a separate liquid source.

Typically, liquid is supplied into the channel 5 at a constant flow rate so that the liquid exits the needle 1 at the outlet end 4 in a continuous stream.

The body 2 comprises a plurality of axially extending reinforcing ribs 2*a* on the exterior of the body 2, although the presence of the ribs is not an essential requirement of the invention.

A cylindrical nozzle portion 7 is provided at the outlet end 4 of the needle 1. The nozzle portion 7 has a uniform diameter portion 7*a* and a chamfered portion 7*b* comprising a frustoconical surface or chamfer 8 converging towards the opening of the channel 5 at the outlet end 4 of the body 2. The chamfered portion 7*b* provides a reduction of thickness of the nozzle material towards the opening of the channel 5 so that (as shown in FIG. 3*a*) an end surface 9 is formed at the tip of the nozzle portion 7. The end surface 9 is narrower than a respective end surface of a similar un-chamfered nozzle portion. It has been found that the narrower end surface 9 reduces the area of surface contact between a liquid droplet and the material of the nozzle portion 7. The consequent lower surface attraction between the droplets at the outlet opening provides for the formation of smaller droplets the outlet end 4 compared to droplets formed at an un-chamfered nozzle portion thus providing more accurate filling of a dosage container or any other vessel for any suitable purpose. Also it has been found that such a chamfered nozzle portion 7 reduces the chance of separation of the droplets from the nozzle portion 7. Such droplets of liquid form at the needle tip at the time when the liquid stream is shut off. At this time, depending on the construction of the filling system, the liquid remaining in the liquid passageway between the shut off location and the outlet end of the needle either exits the needle through the needle outlet end or is drawn back into the liquid passageway by a pump, or a combination of the above two possibilities may occur. In any of those events however droplets of liquid form at the outlet opening of the needle and they may or may not separate from the needle tip. Also, at the end of those events, it is not uncommon that a droplet of liquid remains attached to the needle which is subsequently discharged into a next dosage container. Although the needle of the invention does not absolutely prevent any droplets from getting into the dosage container, it provides for increased accuracy of a fill due to the reduced size of the droplets and a smaller chance of separation. By selection of the width of the end surface 9, droplet sizes from a plastics needle can be matched to those obtainable from a prior art stainless steel needle of comparable bore size. By this means, a disposable, inexpensive plastics needle may be used in a filling system in place of a relatively more expensive stainless steel needle, and the plastic needle can be disposed of after use, reducing the need for costly and time consuming cleaning procedures. The chamfered plastic needle, though necessarily having a thicker wall along its length for a given bore size than a comparable metal needle, will nevertheless allow comparably sized droplets to form at the needle's outlet. For example, in an existing stainless steel needle having an internal bore diameter of 3.1 mm the wall thickness and, accordingly, the width of the end surface at the outlet of the stainless steel needle may be between 0.5 mm and 1 mm. In an exemplary 40 mm long plastics needle of a similar bore diameter (3.2 mm) the wall thickness and the width of the end surface is about 1.5 mm. Table 1 shows examples of wall thicknesses selected for other 40 mm long plastics needle depending on the diameter of the through channel of the needle:

TABLE 1

| Internal diameter, mm | Wall thickness, mm |
|---|---|
| 0.8 | 2.62 |
| 1.2 | 2.42 |
| 1.6 | 2.21 |

Without the above described wall-thickness reduction significant difference in droplet size could be expected. However, the provision of the chamfer at the plastics needle outlet end can reduce the end surface to any desired width, e.g. 0.5 mm like that of the corresponding stainless steel needle, or even less.

It will be appreciated that the body 2 can be configured in any suitable manner as long as there is provided a region with reduced material thickness of the body 2 at the outlet end 4 of the needle towards the outlet tip, so as to define an end surface about the opening of the channel, the area of the end surface which comes into contact with droplets in use being smaller than the wall thickness of the needle body. Alternatively, a sharp rim surrounding the channel opening may be defined by further reducing the material thickness at the surface. Such an arrangement causes reduction of the contact surface between a droplet and the needle and consequently reduces the attraction between the droplet and the needle and provides for formation of smaller droplets compared to needles without such body thickness reduction.

As shown in FIG. 5, an alternative inlet fitting 10 may be provided at the inlet end 3 of the needle 1. The inlet fitting 10 differs from the inlet fitting 6 in that it comprises a ribbed connector portion 10*a*.

FIGS. 6 and 7 show needles 100 and 110 respectively which represent the most preferred embodiments of the invention. Each of these needles 100 and 110 has a chamfer similar to the chamfer 8 and differ from the needle 1 primarily in their bore sizes and in not having reinforcing ribs.

FIGS. 8 and 8*a* show two needles 1 connected to a filling system via two respective first discharge manifolds 12. It will be appreciated that the needle of the invention may be used with various liquid sources and that any required number of needles may be connected to the liquid source in a filling system. For example, a filling system may comprise a first bag 11, into which liquid is supplied via a supply manifold 13. The bag 11 has a handle 14 for hanging the bag 11 at a level higher than the level at which filling of containers via the needles is carried out. Liquid flow in the manifolds 12 is controlled by lock clips 15 fastenable to flexible regions 12*a* of the manifolds 12. The supply manifold 13 of the bag 11 is connected to a larger supply bag 16 via a second discharge manifold 17. The larger bag 16 has a supply manifold 18 and a lock clip 19, both similar to those described with reference to the first bag 11. The discharge manifolds 17 and 15 may also include pumps 20, tubing connectors 21 and filters 22. In other filling systems the large bag 16 may be omitted.

Tests have been conducted to compare filling performances of a prior art stainless steel filling needle and a plastics needle according to the invention over a pre-determined number of fills for a predetermined nominal volume of liquid, the needles having comparable bore sizes and the flow rates being comparable. Each of FIGS. 9 and 10 shows comparative graphs illustrating fluctuations from nominal value of liquid volumes delivered by a prior art stainless steel needle and a plastics needle of the invention during about one hundred fills. During each test a vial was first placed under the outlet end of a first needle, for example a stainless steel needle. Next, the liquid flow was turned on and the vial was filled in accordance with a pre-set nominal volume. After that the liquid flow was shut off and the residual liquid in the needle was allowed to behave in accordance with the following expected possibilities: exit the needle through the needle outlet end; or be drawn back into the liquid passageway by a pump or a vacuum created during the shut off, or a combination of the above two possibilities. It was also expected that in any of those events one or more droplets of liquid could form at the outlet opening of the needle which may or may not separate from the needle tip. Also, at the end of those events, it was envisaged that a droplet of liquid could remain attached to the needle, which droplet was expected to be subsequently discharged into a next vial. The above steps were repeated for a hundred of vials and then the needle was changed to a second needle, e.g. a plastics needle and the test was repeated in respect of the latter needle.

FIG. 9 shows a graph comparing the performance of a plastics needle with an internal diameter (bore) of 3.2 mm (using the needle embodiment of FIG. 6) and an end surface of about 0.42 mm with a stainless steel needle having an internal diameter (bore) of 3.1 mm and a wall thickness of about 0.5 mm in filling a nominal volume of 5 ml; and FIG. 10 is a graph comparing the performance of a plastics needle having an internal diameter of 1.2 mm (using the needle embodiment of FIG. 7) and an end surface of about 0.75 mm with a stainless steel needle having an internal diameter of 1.1 mm and a wall thickness of about 0.5 mm in filling a nominal volume of 1 ml. The difference of 0.1 mm between the bore sizes in the pairs of needles selected for the comparative test occurred because of non-availability at the time when the tests were conducted of plastics and stainless steel needles having identical internal bore diameters. This difference however is regarded as being insignificant in the present tests since the accuracy of a particular fill depends primarily on the size of the droplets of liquid formed at the time when the liquid flow is shut off which droplets subsequently fall into the vial.

The graphs show that the difference between volume fluctuations achieved by the plastics needles and by the stainless steel needles are so small that they can be disregarded as falling within measurement tolerances, thus confirming that performance of a plastics filling needle according to the invention is not in any way inferior to the performance of a known stainless steel filling needle. In particular, the following mean fluctuations were recorded:

| | |
|---|---|
| Plastics needle, 3.2 mm internal bore diameter | 0.0230 ml; |
| Stainless steel needle, 3.1 mm internal bore diameter | 0.0202 ml; |
| Plastics needle, 1.2 mm internal bore diameter | 0.0044 ml; and |
| Stainless steel needle, 1.1 mm internal bore diameter | 0.0031 ml. |

Furthermore, since the bore size of the plastics needle used in each of the tested needle pairs was by 0.1 mm larger than that of the stainless steel needle, it is believed that if the internal diameters of the compared needles were identical, the difference in the volume fluctuations would be even smaller.

It will be appreciated that the needle is not limited to use with only the above described bags, and indeed, can be connected to any suitable source of liquid.

It is thought that the present invention and its advantages will be understood from the foregoing description and it will be apparent that various changes may be made thereto without departing from the scope of the invention, the forms hereinbefore described being merely preferred or exemplary embodiments thereof.

The invention claimed is:

1. A needle for transfer of liquid comprising:

an elongate body having a liquid inlet end, a liquid outlet end and a through passage defined by a wall and extending between the ends, the body comprising a tip portion at the outlet end thereof, the wall thickness of which is reduced compared to that of the body, thereby rendering the needle capable of providing for formation of smaller droplets of liquid at the outlet end when the liquid flows from the inlet end towards the outlet end and quicker separation of the droplets from the needle compared to needles without such body thickness reduction;

wherein the needle material is a polymeric material selected from a silicone or a plastics material;

wherein the diameter of the through passage extending between the ends is uniform along the length of the through passage in the body and in the tip portion; the external diameter of the body is uniform along the length of the body; and wherein the ratio between the thickness of the wall material of the body and the diameter of the through passage is selected at least 0.5 or greater thereby providing the needle with the same strength and flexibility characteristics as those of a metal needle having substantially the same body length and substantially the same cross-sectional dimensions of the through passageway.

2. The needle as claimed in claim 1, wherein the reduction of wall thickness at the tip portion of the needle body is provided by forming a chamfer at the tip portion, the chamfer having an outer surface converging towards the opening at the outlet end of the body.

3. The needle as claimed in claim 2, wherein an end surface is formed about the opening at the outlet end so that the needle tip is frusto-conical.

4. The needle as claimed in claim 2, wherein the needle tip has the shape of a sharp rim.

5. The needle as claimed in claim 1, wherein, the needle material is selected from one of polyethylene, polyetherimide, polysulfone and ethylene tetrafluoroethylene.

6. A filling system comprising at least one liquid source vessel having at least one outlet opening, at least one discharge manifold having a first end connected to the outlet opening of the liquid source vessel and a second end connected to the liquid inlet end of a needle, wherein the needle comprises an elongate body having a liquid inlet end, a liquid outlet end and a through passage defined by a wall and extending between the ends, the body comprising a tip portion at the outlet end thereof, the wall thickness of which is reduced compared to that of the body, thereby rendering the needle capable of providing for formation of smaller droplets of liquid at the outlet end when the liquid flows from the inlet end towards the outlet end and quicker separation of the droplets from the needle compared to needles without such body thickness reduction, wherein the needle material is a polymeric material selected from a silicone or a plastics material;

wherein the diameter of the through passage extending between the ends is uniform along the length of the through passage in the body and in the tip portion; the external diameter of the body is uniform along the length of the body; and wherein the ratio between the thickness of the wall material of the body and the diameter of the through passage is selected at least 0.5 or greater thereby providing the needle with the same strength and flexibility characteristics as those of a metal needle having substantially the same body length and substantially the same cross-sectional dimensions of the through passageway; and further wherein the discharge manifold further comprising a liquid flow control means.

7. The filling system as claimed in claim 6 wherein the material of the liquid source vessel, the discharge manifold, the liquid flow control means and the needle is a polymer selected from a silicone or a plastics material.

8. A method of transferring liquid into a vessel comprising the steps of:

a) providing a filling system comprising at least one liquid source vessel having at least one outlet opening, at least one discharge manifold having a first end connected to the outlet opening of the liquid source vessel and a second end connected to the liquid inlet end of a needle, wherein the needle comprises an elongate body having a liquid inlet end, a liquid outlet end and a through passage defined by a wall and extending between the ends, the body comprising a tip portion at the outlet end thereof, the wall thickness of which is reduced compared to that of the body, thereby rendering the needle capable of providing for formation of smaller droplets of liquid at the outlet end when the liquid flows from the inlet end towards the outlet end and quicker separation of the droplets from the needle compared to needles without such body thickness reduction, wherein the needle material is a polymeric material selected from a silicone or a plastics material;

wherein the diameter of the through passage extending between the ends is uniform along the length of the through passage in the body and in the tip portion; the external diameter of the body is uniform along the length of the body; and wherein the ratio between the thickness of the wall material of the body and the diameter of the through passage is selected at least 0.5 or greater thereby providing the needle with the same strength and flexibility characteristics as those of a metal needle having substantially the same body length and substantially the same cross-sectional dimensions of the through passageway;

b) directing the outlet end of the needle into a vessel; and c) adjusting the liquid flow control means to cause liquid flow from the liquid source vessel through the discharge manifold and through the passage in the needle at a selected flow rate; and d) selecting a liquid source vessel, a discharge manifold, a liquid flow control means and a needle, the liquid source vessel, the discharge manifold, the liquid flow control means and the needle being made form a polymeric material, and prior to step b), subjecting the filling system to sterilisation using gamma-rays, the irradiation dose being selected to provide through-sterilisation of the liquid source vessel, the polymeric material of the discharge manifold, the liquid flow control means and the needle without damaging the polymeric material thereof.

* * * * *